United States Patent [19]

Perregaard et al.

[11] Patent Number: 5,002,948

[45] Date of Patent: Mar. 26, 1991

[54] 3-[4-[4-SUBSTITUTED-1-PIPERAZINYL]-1-BUTYL]-1H-2,3-DIHYDROINDOLES

[75] Inventors: Jens Perregaard, Jaegerspris; John W. Stenberg, Copenhagen, both of Denmark

[73] Assignee: H. Lundbeck A/S, Copenhagen-Valby, Denmark

[21] Appl. No.: 456,938

[22] Filed: Dec. 26, 1989

[30] Foreign Application Priority Data

Dec. 28, 1988 [GB] United Kingdom ............... 8830312

[51] Int. Cl.$^5$ .................. A61K 31/495; C07D 403/06
[52] U.S. Cl. .................... 514/254; 514/253; 544/366; 544/369; 544/373
[58] Field of Search ............. 544/366, 369, 373; 514/253, 254

[56] References Cited

U.S. PATENT DOCUMENTS

| | | | |
|---|---|---|---|
| 3,135,794 | 6/1964 | Archer | 544/373 |
| 3,188,313 | 6/1965 | Archer | 544/373 |
| 3,468,882 | 9/1969 | Laskowski | 544/373 |
| 3,751,417 | 8/1973 | Allen et al. | 544/373 |
| 3,900,495 | 8/1975 | Allen Jr. et al. | 544/373 |
| 4,252,803 | 2/1981 | Webb | 544/373 |
| 4,382,935 | 5/1983 | Buzas et al. | 544/373 |
| 4,452,799 | 7/1984 | Temple, Jr. et al. | 544/373 |
| 4,710,573 | 12/1987 | Strupczewski | 548/371 |
| 4,782,061 | 11/1988 | Kruse et al. | 544/373 |
| 4,831,031 | 5/1989 | Lowe III, et al. | 544/373 |

FOREIGN PATENT DOCUMENTS

| | | | |
|---|---|---|---|
| 2888 | 4/1989 | PCT Int'l Appl. | 544/373 |
| 1075156 | 7/1967 | United Kingdom | 544/373 |
| 1116196 | 6/1968 | United Kingdom | 544/373 |

OTHER PUBLICATIONS

Sterling Drug Inc., Chem. Abst. 60–9293g (1964), Abstract of UK 944,443.
Laskowski, Chem. Abst. 72–43733v (1970) Abstract of Fr. 1,551,082.

Primary Examiner—Cecilia Shen
Attorney, Agent, or Firm—Gordon W. Hueschen

[57] ABSTRACT

The present invention relates to novel piperazinylbutylindoles, -indazoles, the corresponding 2,3-dihydro derivatives and 2-indolones which have been found to have central serotonin activity with preference for the serotonin 5-HT$_{1A}$ receptor.

Compared to the anxiolytic drug buspirone, and other clinically investigated compounds such as ipsapirone and gepirone, most of the present compounds have lower efficacy at the 5-HT$_{1A}$ receptor which implies less side effects related to activation of the receptors.

The invention also includes acid addition salts, methods of preparation, pharmacetical compositions and method of treating CNS disorders occuring in anxiety, depression, aggression and in alcohol abuse, or in states of disease related to the cardiovascular, gastrointestinal and renal systems, by administering the aforementioned derivatives.

Separation and use of the stereo isomers of the 2,3-dihydro derivatives and 2-indolones are also part of this invention.

12 Claims, No Drawings

3-[4-[4-SUBSTITUTED-1-PIPERAZINYL]-1-BUTYL]-1H-2,3-DIHYDROINDOLES

SUMMARY OF THE INVENTION

The novel indoles, indazoles, 2-indolones, and the 2,3-dihydro derivatives thereof are all represented by the following formula I:

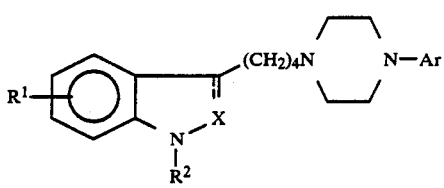

wherein the dotted line indicates an optional bond;

X is CH, CH$_2$, N(H) or C=O;

R$^1$ is hydrogen, halogen, lower alkyl, lower alkenyl, trifluoromethyl, (lower alkyl means 1-6 carbon atoms, branched or unbranched);

R$^2$ is hydrogen, lower alkyl or alkenyl (C$_1$-C$_6$ inclusive, branched or unbranched) optionally substituted with one or two hydroxy groups, any hydroxy group present being optionally esterified with an aliphatic carboxylic acid having from two to twenty-four carbon atoms inclusive, or any of the following acyl groups

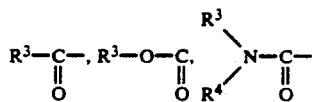

in which R$^3$ and R$^4$ are hydrogen, alkyl (1-20 C-atoms, branched or unbranched, cyclo alkyl (3-6 C-atoms), adamantyl, aralkyl (4-13 C-atoms inclusive);

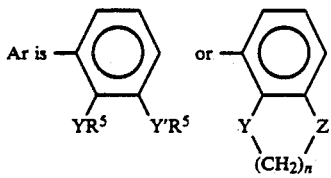

in which Y is O or S; Y' is H, O, S or CH$_2$; Z is O, S or CH$_2$; n is 1, 2 or 3; and R$^5$ is hydrogen, lower alkyl or alkenyl (C$_1$-C$_6$ inclusive, branched or unbranched);

as well as pharmaceutically acceptable acid addition salts and stereo isomers thereof.

BACKGROUND OF THE INVENTION

4-Phenyl-1-piperazinylalkyl-3-indoles have previously been disclosed in the following patents: Fr. No. 1,551082 (Sterling Drug Inc.—1968); U.S. Pat. No. 3,135,794 (Sterling Drug Inc.—1964); GB No. 944,443 (Sterling Drug Inc.—1963) and in the following papers as well: Med. Pharm. Chem. 5, 932-943 (1962), Arch. intern. Pharmacodyn. 157 (1) 67-89 (1965). These patents and papers have focused on 4-phenyl-1-piperazinylethyl-3-indoles with antihistaminergic, sedative, hypotensive and tranquilizing activity, however, without mentioning of serotonergic activity and the diseases where deficits in this neurotransmitter system are involved. The only butyl derivative included in our invention specifically mentioned in the above patents and papers was 3-[b 1-(2-methoxyphenyl)-4-piperazinyl]-4-butylindole (Compound 2a).

In the compounds of formula I the preferred compounds are dihydroindoles, 2-indolones and indazoles with R$^2$ being preferably hydrogen or methyl and R$^1$ hydrogen, halogen or trifluoromethyl. The aromatic substituent Ar is preferably 2-lower alkoxyphenyl, 1,4-benzodioxan-5-yl, or 2,3-dihydro-7-benzofuranyl.

This invention also includes pharmaceutically acceptable salts of the compounds of Formula I formed with non-toxic organic or inorganic acids. Such salts are easily prepared by methods known to the art.—The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly.—Exemplary of such organic salts are those with maleic, fumaric, benzoic, ascorbic, embonic, succinic, oxalic, bis methylene-salicylic, methanesulfonic, ethanedisulfonic, acetic, propionic, tataric, salicylic, citric, glucomic, lactic, malic, mandelic, cinnamic, citraconic, aspartic, stearic, palmitic, itaconic, glycolic, p-aminobenzoic, glutamic, benzene sulfonic and theophylline acetic acids as well as the 8-halotheophyllines, for example 8-bromo-theophylline.—Exemplary of such inorganic salts are those with hydrochloric, hydrobromic, sulfuric, sulfamic, phosphoric and nitric acids. Of course, these salts may also be prepared by the classical method of double decomposition of appropriate salts, which is well-known to the art.

According to the method of the invention, the compounds of Formula I are prepared by (a) reducing the amide carbonyl of a compound of the formula II

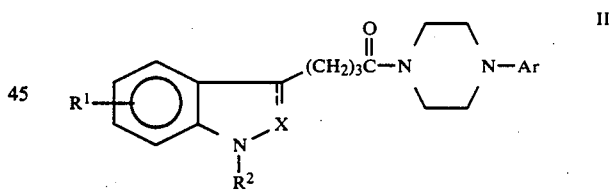

wherein R$^1$, R$^2$, X and Ar are as previously defined;

(b) alkylating, acylating or arylating a compound of the formula III

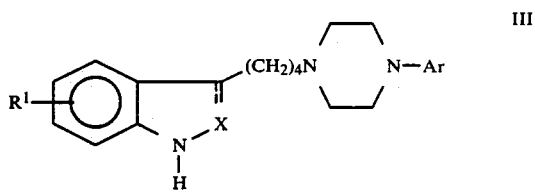

with an alkyl-, acyl- or phenylhalogenide R$^2$X. R$^1$, X and Ar are as previously defined. Acylation of the NH group with a carboxylic acid chloride with subsequent reduction of the amide also gives compounds o structure I;

(c) alkylating an arylpiperazin

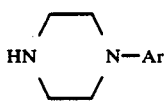

with an alkylating reagent of the following formula IV

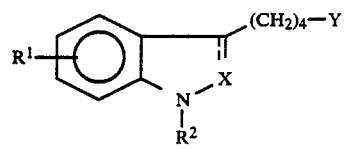

wherein $R^1$, $R^2$ and X are as previously defined, while Y is a leaving group as eg. halogen, mesylate or tosylate;

(d) reducing the 2-3 double bond in an indole or indazole derivative of the following formula V

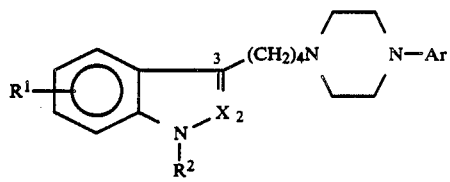

wherein $R^1$, $R^2$, X and Ar are as previously defined;

(e) oxidizing an indole derivative of the formula VI to an 2-indolone derivative of formula VII

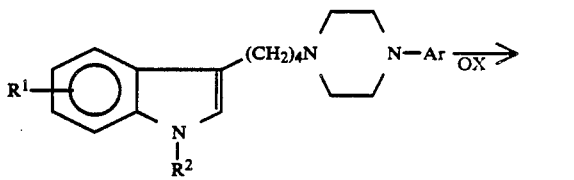

(f) making a ring closure reaction of the hydrazon VIII to the indazole derivative IX

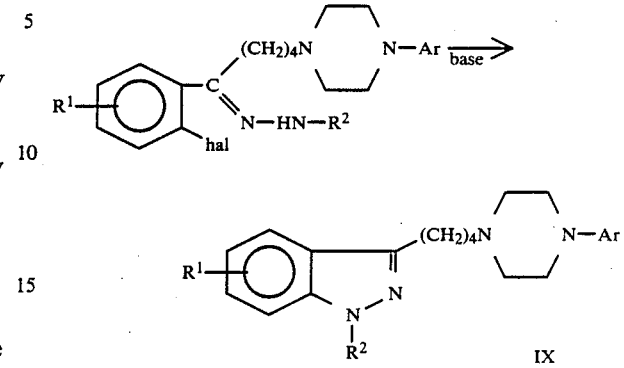

whereupon the compound of Formula I formed is isolated as the free base, or a pharmaceutically acceptable acid addition salt thereof, and if desired, separated in individual optical isomers.

The reduction according to method (a) may preferably be carried out in an inert organic solvent such as diethyl ether or tetrahydrofuran in the presence of lithium aluminium hydride at reflux temperature.

Reduction of the 2-3 double bond of indoles or indazoles according to method (d) is conveniently performed by catalytic hydrogenation in an alcohol with platinum or by hydrocarbon with diborane or a diborane precursor such as the trimethylamine or dimethylsulphide complex in tetrahydrofuran or dioxane from 0° C. to reflux temperature, followed by acid catalyzed hydrolysis of the intermediate borane derivative.

Alkylation of an arylpiperazine according to method (c) is conveniently performed in an inert organic solvent such as a suitably boiling alcohol or ketone, preferably in the presence of a base (potassium carbonate or triethylamine) at reflux temperature.

1-Arylpiperazines are either commercially available or may be prepared according to the methods in Martin et al. *J. Med. Chem.*, 32 1052-1056 (b 1989).

3Indolebutyric acids are convenient starting materials for the preparation of indolebutyric acid amides (formula, II, X=CH) and for alkylating indolebutyl derivatives (formula, IV, X=CH). The butyric acids are prepared according to DE No. 3421,641 A1 or HUN.PAT. No. 187 127.

The carboxylic acids are further reacted according to the following reaction scheme:

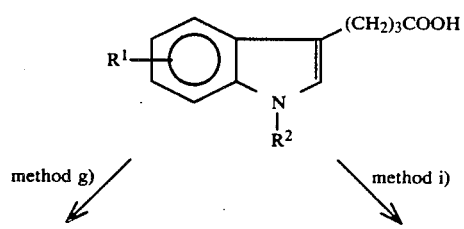

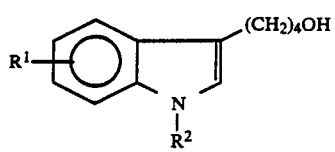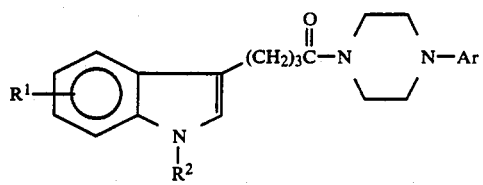

↓ method h)

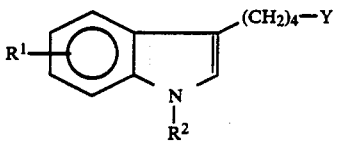

Hydrazones of the general Formula VIII are conveniently obtained according to the following reaction procedure:

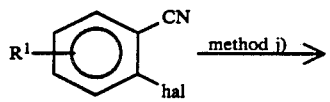

method j) →

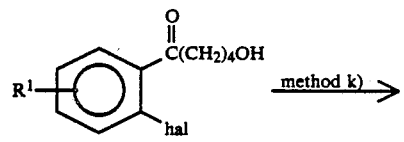

method k) →

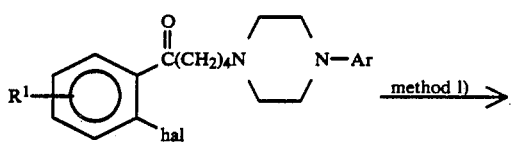

method l) →

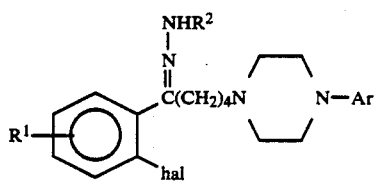

The methods of the invention shall in the following be illustrated by some examples which, however, may not be construed as limiting:

EXAMPLE 1

Methods (i) and (a)

5-Fluoro-3-[4-[4-(2-methoxyphenyl)-1-piperazinyl]-1-butyl]-1 H-indole, 1a

To a solution of 5-fluoro-3-(3-carboxypropyl)-1H-indole (11 g) in 200 ml of dry THF was added 1-(2-methoxyphenyl)piperazine (9.6 g) and subsequently N,N-dicyclohexyl carbodiimide (12.5 g) and 4-(N,N-dimethylamino)pyridine (0.5 g). The mixture was stirred overnight, filtered and the solvent evaporated in vacuo. The remaining oil was dissolved in ethyl acetate (200 ml) and washed with brine (2×10 ml), the organic phase was dried (MgSO4), filtered and finally evaporated leaving 19 g of a viscous oil. The product was eluted through silica gel (900 g) with ethyl acetate yielding 9.8 g of the carboxylic acid amide as an oil.

The amide (9.8 g) in dry THF (100 ml) was added dropwise to a suspension of LiAlH4 (5 g) in dry THF (80 ml). The mixture was refluxed for 2 hours. After cooling in an ice bath, THF containing 10% of water was added dropwise with stirring. Solid NH4Cl (25 g) was added, and the precipitated inorganic salts were filtered off. The solvents were evaporated and the remaining water was removed by evaporation twice with toluene. The residue (9.2 g) was dissolved in isopropyl ether. The title compound crystallized by refrigeration. Yield: 7.4 g. MP 98°-100° C.

In a similar manner was also prepared:

6-Chloro-3-[4-[4-(2-methoxyphenyl)-1-piperazinyl]-1-butyl]-1H-indole, 1b. MP 135°-138° C.

EXAMPLE 2

Methods (g) and (c)

3-[4[4-(2-methoxyphenyl)-1-piperazinyl]-1-butyl]-1H-indole, 2a

A solution of 3-(3-carboxypropyl)-1H-indole (20 g) in diethyl ether (300 ml) was added dropwise to a suspension of LiAlH4 (12 g) in diethyl ether (200 ml). The reaction mixture was refluxed for 2 hours and cooled to 10° C. The mixture was hydrolyzed by careful addition of water and was finally filtered. The filter cake was thoroughly washed with THF. Evaporation of the solvents yielded 17 g of the crude butanol derivative.

To a solution of the butanol (8 g) in dichloromethane (200 ml was added triethylamine (9 ml). After cooling to 5° C. methanesulfonylchloride (4.5 ml) in dichloromethane (35 ml) was added dropwise at 5°-10° C. Stirring was continued for another ½ hour. The mixture was dissolved in ethyl acetate/dichloromethane (1:1) and filtered through silica gel. The solvents were evaporated affording 9 g of the methansulfonic acid ester.

To a solution of the ester (8 g) in dry acetone (100 ml) were added 1-(2-methoxyphenyl(piperazine (5.5 ) and K2CO3 (6 g anh.). The mixture was refluxed for 24 hours. The acetone was evaporated and the residue dissolved in diethylether and water. The water phase was made acidic by addition of acetic acid, and the organic phase was separated and discarded. The water phase was made alkaline (pH=10) by addition of NH4OH. Extraction with ethyl acetate (2×100 ml) and subsequent working up of the combined organic phases yielded 10 g of crude product.

The pure title compound 2a crystallized from diethyl ether. MP: 113°–115° C.

In a similar manner were also prepared:
3-[4-[4-(2,3-dihydro-7-benzofuranyl)-1-piperazinyl]-1-butyl]-1H-indole, 2b. MP: 136°–138° C.
3-[4-[4-(1,4-benzodioxan-5-yl)-1-piperazinyl]-1-butyl]-1H-indole, oxalate 2c. MP: 174°–177° C.
3-[4-[4-(1,4-benzodioxan-5-yl)-1-piperazinyl]-1-butyl]-5-fluoro-1H-indole, oxalate 2d. MP: 188° C.
3-[4-8 4-(2,3-dihydro-7-benzofuranyl)-1-piperazinyl]-1-butyl]-5-fluoro-1H-indole, 2e, MP: 102°–103° C.

EXAMPLE 3

Method (d)

3-[4-[4-(2-methoxyphenyl)-1-piperazinyl]-1-butyl]-1H-2,3-dihydroindole, dioxalate, 3a.

Compound 2a (10 g) and borane/trimethylamine complex (24 g) were dissolved in dioxan (160 ml). Conc. hydrochloric acid (18 ml) was added at 25°–30° C. during 30 min. The mixture was then slowly heated to reflux temperature and refluxed for 1 hour. After cooling to room temperature 6M hydrochloric acid (60 ml) was added, and the mixture was further refluxed for ½ h. After cooling diethyl ether (200 ml) and dil. NaOH solution (200 ml) were added. The organic phase was separated. The basic product was extracted into 0.2M methanesulfonic acid solution. The acidic water phase was made alkaline (NH4OH) and the product was extracted with diethyl ether. The organic phase was evaporated, dried (MgSO4) and filtered. Finally the ether was evaporated.

The title compound 3a crystallized as a dioxalate salt from a boiling ethanol/acetone mixture by addition of oxalic acid. Yield: 11.2 g (75%). MP: 169°–170° C.

In a similar manner were also prepared:
3-[4-[4-(2-methylthiophenyl)-1-piperazinyl]-1-butyl]-1H-2,3-dihydroindole, dioxalate, 3b, MP: 152° C.
3-[4-[4-(2-ethoxyphenyl)-1-piperazinyl]-1-butyl]-1H-2,3-dihydroindole, dioxalate 3c, MP: 93°–94° C.
3-[4-[4-(2-isopropyloxyphenyl)-1-piperazinyl]-1-butyl]-1H-2,3-dihydroindole, dioxalate, 3d, MP: 176°–177° C.
5-chloro-3-[4-[4-(2-methoxyphenyl)-1-piperazinyl]-1-butyl]-1H-2,3-dihydroindole, oxalate, 3e, MP: 137°–138° C.
6-chloro-3-[4-[4-(2-methoxyphenyl)-1-piperazinyl]-1-butyl]-1H-2,3-dihydroindole, trihydrochloride hydrate, 3f, MP: 168°–172° C.
5-fluoro-3-[4-[4-(2-methoxyphenyl)-1-piperazinyl]-1-butyl]-1H-2,3-dihydroindole, 3g, MP: 70°–73° C.
3-[4-[4-(2,3-dimethoxyphenyl)-1-piperazinyl]-1-butyl]-1H-2,3-dihydroindole, 3h, MP: 111°–112° C.
3-[4-[4-(2,3-dihydro-7-benzofuranyl)-1-piperazinyl]-1-butyl]-1H-2,3-dihydroindole, dioxalate, 3i, MP: 81°–83° C.
3-[4-[4-(1,4-benzodioxan-5-yl)-1-piperazinyl]-1-butyl]-1H-2,3-dihydroindole, dioxalate, 3j, MP: 168°–169° C.
3-[4-[4-(1,4-benzodioxan-5-yl)-1-piperazinyl]-1-butyl]-5-chloro-1H-2,3-dihydroindole, oxalate, 3k, MP: 143° C.
3-[4-[4-(1,4-benzodioxan-5-yl)-1-piperazinyl]-1-butyl]-5-fluoro-1H-2,3-dihydroindole, dioxalate, 3l, MP: 163° C.
3-[4-[4-(2,3-dihydro-7-benzofuranyl)-1-piperazinyl]-1-butyl]-5-fluoro-1H-2,3-dihydroindole 3m, MP: 59° C.

EXAMPLE 4

3-[4-[4-(2-hydroxyphenyl)-1-piperazinyl]-1-butyl]-1H-2,3-dihydroindole, 4a

A mixture of 4 g of Compound 3a and 40 g of pyridine hydrochloride was heated to 190°–200° C. under a nitrogen atmosphere for 1.5 hours. After cooling to room temperature dil. NH4OH and ethyl acetate were added. The organic phase was separated, dried (MgSO4), filtered, and ethyl acetate evaporated. The remaining oil crystallized from isopropyl ether, yielding 2.1 g of the title compound 4a. MP: 87°–88° C.

EXAMPLE 5

Method (b)

1-Acetyl-3-[4-[4-(2-methoxyphenyl)-1-piperazinyl]-1-butyl]-1H-2,3-dihydroindole, oxalate, 5a.

To a solution of compound 3a (3 g) and triethylamine in dichloromethane (50 ml) was added acetylchloride (1 ml) in dichloromethane (10 ml) at room temperature during 10 minutes. After stirring for 2 hours the mixture was poured into dil. NH4OH. The dichloromethane phase was separated, dried (MgSO4), filtered and evaporated. Column chromatography on silica gel (eluted with 4% triethylamine in ethyl acetate) yielded 2.5 g of an oil.

The title compound 5a was isolated as an oxalate salt, MP: 115°–117° C.

EXAMPLE 6

Method (b)

3-[4-[4-(2-methoxyphenyl)-1-piperazinyl]-1-butyl]-1-methyl-1H-2,3-dihydroindole, oxalate, 6a.

Compound 3a (7 g), triethylamine (8 ) and ethyl chloroformate (5 ml) were mixed in ice cooled dichloromethane (100 ml). After refluxing for 5 hours the reaction mixture was washed with 0.5M NH4OH solution (2×50 ml), the organic phase was separated, dried (MgSO4) and the solvent evaporated yielding 8 g of crude carbamate.

The crude product in dry diethyl ether (100 ml) was added dropwise to an ice cooled suspension og LiAlH4 in dry diethyl ether (200 ml). After 2 hours of reflux the mixture was carefully hydrolysed. The solid material was filtered off and washed with dichloromethane. The combined organic phases were dried (MgSO4) and the solvents were evaporated affording 6.2 g of the title compound as an oil. The oxalate salt 6a was precipitated in acetone. MP: 117°–120° C.

EXAMPLE 7

Resolution of Compound 3a
(+)-3-[4-[4-(2-methoxyphenyl)-1-piperazinyl]-1-butyl]-1H-2,3-dihydroindole, 7a
(−)-3-[4-[4-(2-methoxyphenyl)-1-piperazinyl]-1-butyl]-1H-2,3-dihydroindole, 7b Compound 3a (55 g) was dissolved in acetone (600 ml). At reflux temperature was added (+)-O,O-dibenzoyl tartaric acid (85 g). The mixture was allows to cool and left at room temperature for 4 hours. The precipitated salt was filtered off. Yield: 53 g (Frakt.I). The remaining solution was evaporated and, subsequently, dil. NH4OH and diethyl ether were added. The organic phase was separated, dried (MgSO4), filtered, and the ether evaporated. To 14 g of the remaining oil was added (−)-O,O-dibenzoyl tartaric acid (21 g) in refluxing acetone (200 ml). The mixture was allowed to cool and left at room temperature for 4 hours. The precipitated salt was filtered off. Yield: 20 g (Frakt.II).

Frakt.I (31 g) was dissolved in boiling acetone (300 ml). After cooling and stirring for 3 hours at room temperature the precipitated salt was filtered off. Yield: 20 g. MP: 98° C. The thus obtained salt was added to a mixture of dil. NH$_4$OH and diethyl ether. The organic phase was separated, dried (MgSO$_4$) and the ether evaporated leaving 10 g. of an oil. The oil was dissolved in acetone (50 ml), and oxalic acid (3.5 g) was added. The crystalline precipitate was filtered off and dried. Yield: 8.1 g $[\alpha]D = +7,39°$ (c=1, methanol). The oxalate salt was added to dil. NH$_4$OH and diethyl ether. The organic phase was separated, dried (MgSO$_4$), filtered, and the solvent evaporated. The remaining oil was dissolved in cyclohexane and left over night in a refrigerator. The precipitated crystalline product was filtered off, yielding 2.5 g of the title (+)-isomer, 7a. MP: 68° C. $[\alpha]D = +41,50°$ (c=1, methanol).

Similarly the (−)-isomer, 7b, was obtained from Frak.II. Yield: 1.6 g. MP: 68° C. $[\alpha]D = -39,27°$ (c=1, methanol.

In a similar way Compound 3j was resolved:
(+)-3-[4-[4-(1,4-benzodioxan-5-yl)-1-piperazinyl]-1-butyl]-1H-2,3-dihydroindole, dioxalate, 7c, MP: 169° C. $[\alpha]D = +1,93°$ (c=1, water).
(−)-b 3-[4-[4-(1,4-benzodioxan-5-yl)-1-piperazinyl]-1-butyl]-1H-2,3-dihydroindole, dioxalate, 7d, MP: 169° C. $[\alpha]D = -2,02°$ (c=1, water).

EXAMPLE 8

Methods (g), (h) and (e)

3-[4-[4-(2-methoxyphenyl)-1-piperazinyl]-1-butyl]-1H-2,3-dihydroindol-2-on, dihydrochloride. 8a To 3-indolyl-4-butan-1-ol (prepared as in Example 2) (14 g) in 95% tert.-butanol (500 ml) was added N-bromosuccinamide (16 g) during 1.5 in small portions at room temperature. After stirring for another ½ hour 200 ml of ethanol and 20 ml of water were added. The mixture was stirred with NaBH$_4$ (4 g) for 1.5 h. The organic solvents were evaporated and the 2-indolonbutanol was extracted with ethyl acetate. The organic phase was dried (MgSO$_4$), and the solvent subsequently evaporated yielding 11 g of crude product. The pure compound crystallized from isopropylether. MP: 82° C.

To the 2-indolon derivative (5 g) from above was added triethylamine (5 ml) in dichloromethane (100 ml). The mixture was cooled to 5° C., and methanesulfonylchlorid (2.5 ml) in dichloromethane (25 ml) was added dropwise during 20 minutes. The mixture was stirred for another hour at room temperature. Water (200 ml) was added and the organic phase was separated, dried (MgSO$_4$), and the dichloromethane was evaporated yielding 7 g of an oil.

To this oil in acetone (150 ml) were added 1-(2-methoxyphenyl)piperazine (7 g) and K$_2$CO$_3$ (5 g). The mixture was refluxed for 17 h. The precipitated inorganic salts were filtered off and the acetone was subsequently evaporated leaving 3 g of crude title compound. The dihydrochloride salt 8a was precipitated from acetone. Yield: 1.9 g. MP: 181°–184° C.

EXAMPLE 9

Methods (c) and (f)

3-[4-[4-(2-methoxyphenyl)-1-piperazinyl]-1-butyl]-5-trifluoromethyl-1H-indazole, oxalate. 9a To a suspension of Mg-turnings (27 g) in dry tetrahydrofuran (100 ml) covered with N$_2$ was added ethylbromide (28 g) in dry tetrahydrofuran (100 ml) during 45 minutes at reflux temperature. After stirring for another hours, 4-chloro-1-butanol (44 g) in dry tetrahydrofuran (100 ml) was added during 1 hour at reflux temperature. After stirring for another ½ hour the reaction mixture was cautiously added to a solution of 2-chloro-5-trifluoromethylbenzonitrile (40 g) in dry tetrahydrofuran (150 ml). The temperature was kept below 35° C. After stirring for 1 hour the reaction mixture was poured onto ice (500 g) and conc. HCl (100 ml). Ether (200) was added, and the mixture was vigorously stirred and then slowly allowed to reach room temperature. The organic phase was finally separated, dried (MgSO$_4$), and the solvents evaporated leaving 44 g of an oil which was purified by colomn chromatography (eluted with dichloromethane/ether 3:1). Yield: 11 g of 4-(2-chloro-5-trifluoromethylphenyl)-4-oxopentan-1-ol.

The pentanol derivative (11 g) was dissolved in dichloromethane (100 ml) containing triethylamine (8 ml). After cooling of the mixture (10° C.) methanesulphonyl chloride (4 ml) dissolved in dichloromethane (20 ml) was added dropwise during ½ hour. Upon another ½ h of stirring, water (300 ml) was added, and the organic phase subsequently separated. After drying (MgSO$_4$), filtering and evaporation of the organic solvents 14 g of 4-(2-chloro-5-trifluoromethylphenyl)-4-oxo-1-pentyl methanesulphonate were isolated.

To the methansulphonic acid ester (14 g) in acetone (200 ml) were added 1-(2-methoxyphenyl)piperazine (12 g) and K$_2$CO$_3$ (6 g). This mixture was heated at reflux temperature for 24 hours. Inorganic salts were filtered off and the acetone evaporated. The resulting oil was purified by elution (ethyl acetate/n-heptane/triethylamine 60:40:4) through silica gel. 17 g of 1-[4-(2-chloro-5-trifluoromethylphenyl)-4-oxo-1-phenyl]-4-(2-methoxyphenyl(piperazine was thus isolated as an oil.

To this piperazinyl derivative (9 g) in ethanol (100 ml) was added hydrazine hydrate (20 ml). The mixture was refluxed for 5 h. After evaporation the remaining oil was purified by column chromatography on silica gel leaving 9 g of a reasonably pure hydrazone derivative, which was dissolved on DMF (70 ml). Potassium t-butoxide (5 g) was added by portions during ½ h. After heating at 50° C. for 2 h, ether (200 ml) and saturated NH$_4$Cl solution (200 ml) were added. The organic phase was separated, dried (MgSO$_4$), filtered, and the organic solvent evaporated.

The remaining oil was purified by column chromatography (eluted with 4% triethylamine in ethyl acetate) on silica gel, yielding 3.4 g of the title compound 9a as an oil. An oxalate salt crystallized from acetone. MP: 163°–165° C. Some of the compounds of Formula I have been tested according to established and reliable pharmacological tests as follows:

INHIBITION OF $^3$H-8-OHDPAT BINDING TO SEROTONIN 5-HT$_{1A}$ RECEPTORS IN A RAT BRAIN IN VITRO

By this method the inhibition by drugs of the binding of $^3$H-8-OHDPAT (1 nM) to serotonin 5-HT$_{1A}$ receptors in membranes from rat brain minus cerebellum is determined in vitro.

Procedure

Male Wistar (Mol:Wist) rats (125–250 g) are sacrificed and the brain is dissected and weighed. The brain tissue minus cerebellum is homogenized (Ultra Turrax, 20 sec) in 10 ml of ice cold 50 mM Tris buffer pH 8.0 (at 25° C.) containing 120 mM NaCl, 4 mM $CaCl_2$ and 4 mM $MgCl_2$. The homogenate is centrifuged at 20,000 g for 10 min at 4° C. The pellet is homogenized in 10 ml of buffer and incubated at 37° C. for 10 min. The homogenate is centrifuged as above and the pellet is homogenized in 100 vol (w/v) ice cold buffer containing 10 82 M of parglyine.

Incubation tubes kept on ice in triplicate receive 100 µl of drug solution in water (or water for total binding) and 1000 µl of tissue suspension (final tissue content corresponds to 10 mg original tissue). The binding experiment is initiated by addition of 100 µl of $^3$H-8-OHDPAT (final concentration 1 nM) and by placing the tubes in a 37° C. water bath. After incubation for 15 min the samples are filtered under vacuum (0–50 mBar) through Whatman GF/F filters (25 min). The tubes are rinsed with 5 ml ice cold 0.9% NaCl which are then poured on the filters. Thereafter, the filters are washed with 2×5 ml 0.9% NaCl. The filters are placed in counting vials and 4 ml of appropriate scintillation fluid (e.g. Picofluor TM 15) are added. After shaking for 1 h and storage 2 h in the dark the content of radioactivity is determined by liquid scintillation counting. Specific binding is obtained by subtracting the nonspecific binding in the presence of 10 µM of 5-HT.

For determination of the inhibition of binding five concentrations of drugs covering 3 decades are used.

The measured cpm are plotted against drug concentration on semilogarithmic paper, and the best fitting s-shape curve is drawn. The $IC_{50}$-value is determined as the concentration, at which the binding is 50% of the total binding in control samples minus the nonspecific binding in the presence of 10 µM of 5-HT.

$^3$H-8-OHDPAT from Amersham International plc. England. Specific activity approximately 200 Ci/mmol).

INHIBITION OF 5-METHOXY-N,N-DIMETHYLTRYPTAMINE INDUCED 5-HT SYNDROME IN RATS

The so-called 5-HT syndrome is a characteristic behaviour pattern which is induced by 5-HT agonists with effects on 5-HT, possibly $5-HT_{1A}$ receptors, although lack of specific antagonists make it difficult to evaluate specificity (Smith, L. M. and S. J. Peroutka, Pharmacol. Biochem. & Behaviour 24, 1513–1519, 1986; Tricklebank, M. et al., Eur. J. Pharmacol. 117, 15–24, 1985).

Procedure

Male Wistar rats (Mol:Wist) weighing 170–240 g are used. Test substrate is injected subcutaneously 30 min. before 5-methoxy-N,N-dimethyltryptamine 5 mg/kg, s.c. Four rats are used for each dose. A control group pretreated with saline is included each test day. Ten, 15 and 20 min later the rats are observed for presence of serotonin (5-HT) syndrome: (1) forepaw treading ("piano playing"), (2) head weaving and (3) hindleg abduction. Further, flat motility is scored. Each part of the syndrome is scored as follows: marked effect (score 2), weak syndrome (score 1) and no effect (score 0). The scores of the three observation times are added. Thus the maximum obtainable score for four rats is 24. The effect of the test substance is expressed as per cent inhibition relative to the control group.

The per cent inhibition of the piano playing syndrome is used as the response, and $ED_{50}$ values are calculated by log-prohibit analysis.

ANTAGONISM OF THE DISCRIMINATIVE STIMULUS PROPERTIES INDUCED BY 8-OHDPAT IN RATS.

This test model is used to determine the antagonist effects of a test compound on $5-HT_{1A}$ receptors in vivo. A related method is described by Tricklebank, M. D., J. Neill, E. J. Kidd and J. R. Fozard, Eur. J. Pharmacol. 133, 47–56, 1987; Arnt. J., Pharmacology & Toxicology 64, 165–172, 1989.

Procedure

Male Wistar rats are trained to discriminate between 8-OHDPAT (0.4 mg/kg, i.p., 15 min. pretreatment) and physiological saline in operant chambers equipped with two response levers. Between the levers a dipper is placed, where water rewards (0.1 ml) are presented. The rats are water deprived for at least 24 h and work in a fixed ratio (FR) schedule (final FR=32).

Following 8-OHDPAT administration responding is reinforced only on a designated (drug) lever, whereas responding on the opposite lever has no consequences. Following saline administration responding is reinforced on the lever opposite to the drug lever. Drug and saline trials alternate randomly between training days, although the same treatment is given maximally at 3 consecutive days. The level of discrimination accuracy is expressed as the per cent drug responses and is calculated as the number of correct responses × 100 divided by the sum of the correct and incorrect responses before the first reward. When stable occuracy (mean correct responding=90 per cent; individual rats at least 75 per cent correct responding) is obtained test sessions are included between training days. Test compound is injected s.c. at appropriate time before 8-OHDPAT and the test begins 15 min after 8-OHDPAT injection. The test trial is terminated when a total of 32 responses are made on either lever or when 20 min have elapsed. No reward is given and the rats have free access to water for 20–30 min after the test. The effects are expressed as per cent inhibition of drug responding. Only results from rats making at least 10 responses on one lever are included in data analysis. Furthermore, only test sessions in which at least half of the rats respond are included.

The per cent inhibition of drug response obtained for each dose of test compound is used to calculate $ED_{50}$ values by log-probit analysis.

GENERALIZATION TO DISCRIMINATIVE STIMULUS PROPERTIES INDUCED BY 8-OHDPAT IN RATS.

This test model is used to determine the agonist effects of a test compound on $5-HT_{1A}$ receptors in vivo. A related method is described by Tricklebank, M. D., J. Neill, E. J. Kidd and J. R. Fozard, Eur. J. Pharmacol. 133, 37–56, 1987; Arnt, J., Pharmacology & Toxicology 64, 165–172, 1989.

Procedure

The procedure is the same as for the antagonism test mentioned above, except that the test compound is substituted for 8-OHDPAT and injected s.c. usually 30 minutes or 45 minutes respectively before beginning of the test.

The per cent drug response obtained for each dose of test compound is used to calculate $ED_{50}$ values by log-probit analysis.

The results obtained will appear from the following tables 1 and 2;

TABLE I $^3H$ 8-OH DPAT BINDING DATA

| Compound No. | $IC_{50}$ (n mol) | Compound No. | $IC_{50}$ (n mol) |
|---|---|---|---|
| 1a | 11 | 3j | 3.3 |
| 1b | 10 | 3k | 7.6 |
| 2a | 17 | 3l | 4.4 |
| 2b | 14 | 3m | 5.7 |
| 2c | 5.7 | 4a | 17 |
| 2d | 3.7 | 5a | 35 |
| 2e | 15 | 6a | 43 |
| 3a | 14 | 7a | 13 |
| 3b | 14 | 7b | 8.6 |
| 3c | 11 | 7c | 3.5 |
| 3d | 17 | 7d | 3.1 |
| 3e | 9.2 | 8a | 51 |
| 3f | 5.8 | 9a | 8.6 |
| 3g | 17 | buspirone | 66 |
| 3h | 90 | gepirone | 310 |
| 3i | 9.4 | isapirone | 17 |

TABLE II

IN VIVO MEASUREMENTS OF 5-$HT_{1A}$ ACTIVITIES

| Compound No. | Inhibition of 5-MeODMT induced 5-HT syndrome | 8-OH DPAT cue antagonism | 8-OH DPAT cue agonism |
|---|---|---|---|
| | $ED_{50}$ (μmol/kg)(sc) | | |
| 3a | 1.9 | 7.2 | >9.2 |
| 3c | 0.48 | 4.8 | >26 |
| 3i | 4.0 | >9.0 | 2.7 |
| 3j | 3.1 | 8.8 | >4.4 |
| 7a | 2.1 | 1.0 | >6.8 |
| 7b | 1.3 | >3.4 | >3.4 |
| buspirone | 4.3 | >0.8 | 0.62 |
| gepirone | 32 | NT | 0.81 |
| ipsapirone | 26 | NT | 1.8 |

The compounds of Formula I and the non-toxic acid addition salts thereof may be administered to animals such as dogs, cats, horses, sheeps or the like, including human beings, both orally and parenterally, and may be used for example in the form of tablets, capsules, powders, syrups or in the form of the usual sterile solutions for injection.—Results upon administration to human beings have been very gratifying.

Most conveniently the compounds of Formula I are administered orally in unit dosage form such as tablets or capsules, each dosage unit containing the free amine or a non-toxic acid addition salt of one of the said compounds in a amount of from about 0.10 to about 100 mg, most preferably, however, from about 5 to 50 mg, calculated as the free amine, the total daily dosage usually ranging from about 1.0 to about 500 mg. The exact individual dosages as well as daily dosages in a particular case will, of course, be determined according to established medical principles under the direction of a physician.

When preparing tablets, the active ingredient is for the most part mixed with ordinary tablets adjuvants such as corn starch, potato starch, talcum, magnesium stearate, gelatine, lactose, gums, or the like.

Typical examples of formulas for composition containing 3-[4[4-(1,4-benzodioxan-5-yl)-1-piperazinyl]-1-butyl]-1H-2,3-dihydroindole (Compound No. 3j) as the active ingredient, are as follows:

(1) Tablets containing 5 milligrams of Compound No. 3j calculated as the free base:
| | |
|---|---|
| Compound No. 3j | 5 mg |
| Lactose | 18 mg |
| Potato starch | 27 mg |
| Saccharose | 58 mg |
| Sorbitol | 3 mg |
| Talcum | 5 mg |
| Gelatine | 2 mg |
| Povidone | 1 mg |
| Magnesium stearate | 0.5 mg |

(2) Tablets containing 50 milligrams of Compound No. 3j calculated as the free base:
| | |
|---|---|
| Compound No. 3j | 50 mg |
| Lactose | 16 mg |
| Potato starch | 45 mg |
| Saccharose | 106 mg |
| Sorbitol | 6 mg |
| Talcum | 9 mg |
| Gelatine | 4 mg |
| Povidone | 3 mg |
| Magnesium stearate | 0.6 mg |

(3) Syrup containing per milliliter:
| | |
|---|---|
| Compound No. 3j | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

(4) Solution for injection containing per milliliter:
| | |
|---|---|
| Compound No. 3j | 50 mg |
| Acetic acid | 17.9 mg |
| Sterile water | ad 1 ml |

(5) Solution for injection containing per milliliter:
| | |
|---|---|
| Compound No. 3j | 10 mg |
| Sorbitol | 42.9 mg |
| Acetic acid | 0.63 mg |
| Sodium hydroxide | 22 mg |
| Sterile water | ad 1 ml |

Any other pharmaceutical tableting adjuvants may be used provided that they are compatible with the active ingredient, and additional compositions and dosage forms may be similar to those presently used for neuroleptics, analgesics or antidepressants.

Also combinations of the compounds of Formula I as well as their non-toxic acid salts with other active ingredients, especially other neuroleptics, thymoleptics, tranquilizers, analgetics or the like, fall within the scope of the present invention.

As previously states, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, pamoates and maleates of the amines of Formula I. Other acids are likewise suitable and may be employed if desired. For example: fumaric, benzoic, ascorbic, succinic, salicyclic, bismethylenesalicyclic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated slat in water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals, involving the neurotransmitter serotoinin, by administering to a living animal body, including human beings, an adequate quantity of a compound of Formula I or a non-toxic acid addition salt thereof. An adequate quantity would be from about 0.001 mg to about 10 mg per kg of body weight per day, and from about 0.003 milligrams to about 7 milligrams/kg of body weight per day.

It is to be understood that the invention is not limited to the exact details of operation or exact compound or compositions shown and described, as obvious modifications and equivalents will be apparent to one skilled in the art.

We claim:

1. A compound selected from those of the following formula:

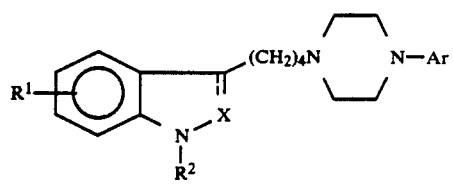

wherein the dotted line indicates an optional bond present only when X is N;

X is $CH_2$, N(H), or C=O;

$R^1$ is hydrogen, halogen, lower alkyl, lower alkenyl, trifluoromethyl, (lower alkyl means 1–6 carbon atoms, branched or unbranched);

$R^2$ is hydrogen, lower alkyl or alkenyl ($C_1$–$C_6$ inclusive, branched or unbranched) optionally substituted with one or two hydroxy groups, any hydroxy group present being optionally esterified with an aliphatic carboxylic acid having from two to twenty-four carbon atoms inclusive, or any of the following acyl groups

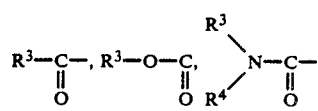

in which $R^3$ and $R^4$ are hydrogen, alkyl (1–20 C-atoms), branched or unbranched, cyclo alkyl (3–6 C-atoms), adamantyl, aralkyl (4–13 C-atoms inclusive);

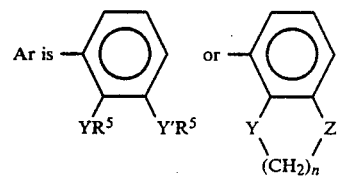

in which Y is O or S; Y' is H, O, S or $CH_2$; Z is O, S or $CH_2$; n is 1, 2 or 3; and $R^5$ is hydrogen, lower alkyl or alkenyl ($C_1$–$C_6$ inclusive, branched or unbranched); and a pharmaceutically acceptable acid addition salt and stereoisomer thereof.

2. A compound according to claim 1, wherein $R^1$ is hydrogen, halogen or trifluoromethyl, $R^2$ is hydrogen or methyl, Ar is 2-lower alkoxyphenyl, 1,4-benzodioxan-5-yl or 2,3-dihydro-7-benzofuranyl, and X is $CH_2$, C=O or N(H): or a pharmaceutically acceptable acid addition salt or stereoisomer thereof.

3. A compound according to claim 1, selected from:
3-[4-[4-(1,4-benzodioxan-5-yl)-1-piperazinyl]-1-butyl]-1H-2,3-dihydroindole
3-[4-[4-(2,3-dihydro-7-benzofuranyl)-1-piperazinyl]-1-butyl]-1H-2,3-dihydroindole
5-Chloro-3-[4-[4-(2-methoxyphenyl)-1-piperazinyl]-1-butyl]-1H-2,3-dihydroindole
3-[4-[4-(2-methoxyphenyl)-1-piperazinyl]-1-butyl]-1H-2,3-dihydroindole
(+)-[4-[4-(2-methoxyphenyl)-1-piperazinyl]-1-butyl]-1H-2,3-dihydroindole
(−)-[4-[4-(2-methoxyphenyl)-1-piperazinyl]-1-butyl]-1H-2,3-dihydroindole
and a pharmaceutically acceptable acid addition salt thereof.

4. 3-[4-[4-(1,4-benzodioxan-5-yl)-1-piperazinyl]-1-butyl]-1H-2,3-dihydroindole;; or a pharmaceutically-acceptable acid addition salt thereof.

5. A pharmaceutical composition useful for the alleviation of CNS disorders involving the neurotransmitter serotonin in unit dosage form comprising, as active ingredient, an amount of a compound as defined in claim 1 which is effective for such purpose, and one or more pharmaceutically-acceptable diluents or carriers.

6. A pharmaceutical composition in unit dosage form according to claim 5, wherein the active ingredient is present in an amount from 0.1 to 100 milligrams per unit dosage.

7. A method for the alleviation of CNS disorders involving the neurotransmitter serotonin in a living animal in need thereof comprising the step of administering to the living animal an effective serotonergic amount of a compound selected from those of the following formula:

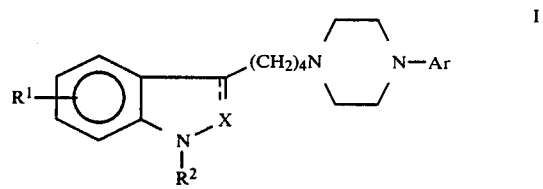

wherein the dotted line indicates an optional bond;
X is CH, $CH_2$, N(H), or C=O;

R¹ is hydrogen, halogen, lower alkyl, lower alkenyl, trifluoromethyl, (lower alkyl) means 1-6 carbon atoms, branched or unbranched);

R² is hydrogen, lower alkyl or alkenyl ($C_1$–$C_6$ inclusive, branched or unbranched) optionally substituted with one or two hydroxy groups, any hydroxy group present being optionally esterified with an aliphatic carboxylic acid having from two to twenty-four carbon atoms inclusive, or any of the following acyl groups

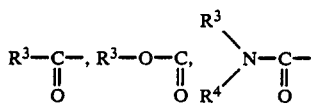

in which R³ and R⁴ are hydrogen, alkyl (1-20 C-atoms), branched or unbranched, cyclo alkyl (3-6 C-atoms), adamantyl, aralkyl (4-13 C-atoms inclusive);

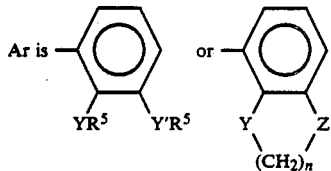

in which Y is O or S; Y' is H, O, S or $CH_2$; Z is O, S or $CH_2$; n is 1, 2 or 3; and R⁵ is hydrogen, loweralkyl, or alkenyl ($C_1$–$C_6$ inclusive, branched or unbranched); and a pharmaceutically-acceptable acid addition salt and stereoisomer thereof.

8. A method according to claim 7, wherein the amount administered is about 0.001 mg to about 10 mg per kg of body weight per day.

9. A method according to claim 7, wherein the amount administered is about 0.003 mg to about 7 mg per kg of body weight per day.

10. A method of claim 7, wherein R¹ is hydrogen, halogen, or trifluoromethyl, R² is hydrogen or methyl, Ar is 2-lower-alkoxyphenyl, 1,4-benzodioxan-5-yl or 2,3-dihydro-7-benzofuranyl, and X is $CH_2$, C=O, or N(H); or a pharmaceutically-acceptable acid addition salt or stereoisomer thereof.

11. A method of claim 7, wherein the compound is selected from

3-[4-[4-(1,4-benzodioxan-5-yl)-1-piperazinyl]-1-butyl]-1H-2,3-dihydroindole

3-[4-[4-(2,3-dihydro-7-benzofuranyl)-1-piperazinyl]-1-butyl]-1H-2,3-dihydroindole 5-Chloro-3-[4-[4-(2-methoxyphenyl)-1-piperazinyl]-1-butyl]-1H-2,3-dihydroindole 3-[4-[4-(2-methoxyphenyl)-1-piperazinyl]-1-butyl]-1H-2,3-dihydroindole (+)-[4-[4-(2-methoxyphenyl)-1-piperazinyl]-1-butyl]-1H-2,3-dihydroindole (−)-[4-[4-(2-methoxyphenyl)-1-piperazinyl]-1-butyl]-1H-2,3-dihydroindole and a pharmaceutically-acceptable acid addition salt thereof.

12. A method of claim 7, wherein the compound is 3-[4-[4-(1,4-benzodioxan-5-yl)-1-piperazinyl]-1-butyl]-1H-2,3-dihydroindole; or a pharmaceutically-acceptable acid addition salt thereof.

* * * * *

UNITED STATES PATENT AND TRADEMARK OFFICE
CERTIFICATE OF CORRECTION

PATENT NO. : 5,002,948

DATED : March 26, 1991

Page 1 of 2

INVENTOR(S) : Jens Perregaard and John W. Stenberg

It is certified that error appears in the above-identified patent and that said Letters Patent is hereby corrected as shown below:

Title Page [56] References Cited, U.S. PATENT DOCUMENTS, line 8; "7/1984" should read -- 6/1984 --
Title Page [30] Foreign Application Priority Data; "8830312" should read -- 8830312.8 --
Title Page [57] ABSTRACT, line 12; "pharmacetical" should read -- pharmaceutical --
Col. 1, line 54; "pharmaceutically acceptable" should read -- pharmaceutically-acceptable --
Col. 1, line 55; "stereo isomers" should read -- stereoisomers --
Col. 2, line 4; "3-[b 1-(2-" should read -- 3-[1-(2- --
Col. 2, lines 12&13; "pharmaceutically acceptable" should read -- pharmaceutically-acceptable --
Col. 2, line 25; "tataric," should read -- tartaric, --
Col. 3, line 34; "an" should read -- a --
Col. 4, line 21; "pharmaceutically acceptable" should read -- pharmaceutically-acceptable --
Col. 4, line 31; "hydrocarbon" should read -- hydroboration --
Col. 4, line 44; "3Indolebutyric" should read -- 3-Indolebutyric --
Col. 5, line 66; "10 ml)," should read -- 100 ml), --
Col. 6, line 51; "(200 ml was" should read -- (200 ml) was --
Col. 6, line 59; "1-(2-methoxyphenyl(piperazine" should read -- 1-(2-methoxyphenyl)piperazine --
Col. 7, line 10; "3-[4-8 4-" should read -- 3-[4-[4- --
Col. 8, line 36; "(8)" should read -- (8 ml) --
Col. 9, line 24; "Frak. II." should read -- Frakt. II. --
Col. 9, line 30; "(-)-b 3-[4-" should read -- (-)-3-[4- --
Col. 9, line 42; "1.5 in" should read -- 1.5 h in --
Col. 9, line 55; "chlorid" should read -- chloride --
Col. 10, line 11; "hours," should read -- 1/2 hour, --
Col. 10, line 23; "colomn" should read -- column --
Col. 10, line 44; "methoxyphenyl(piperazine" should read -- methoxyphenyl)piperazine --
Col. 11, line 15; "10 82 M of parglyine." should read -- 10 $\mu$ M of pargyline. --

UNITED STATES PATENT AND TRADEMARK OFFICE
CERTIFICATE OF CORRECTION

PATENT NO. : 5,002,948

DATED : March 26, 1991

INVENTOR(S) : Jens Perregaard and John W. Stenberg

It is certified that error appears in the above-identified patent and that said Letters Patent is hereby corrected as shown below:

Col. 11, line 59; "substrate" should read -- substance --
Col. 12, line 7; "-prohibit" should read -- -probit --
Col. 12, line 67; "37-56," should read -- 47-56, --
Col. 12, lines 36 and 40 "occuracy" should read --accuracy-- (both occurrences)
Col. 13, approx. line 29; in TABLE I, third column, last line; "isapirone" should read -- ipsapirone --
Col. 13, line 49; "sheeps" should read -- sheep --
Col. 13, line 59; "a" should read -- an --
Col. 13, line 68; "tablets" should read -- tablet --
Col. 14, lines 65 & 66; "salicyclic, bismethylenesalicyclic," should read -- salicylic, bismethylenesalicylic, --
Col. 15, line 6; "slat" should read -- salt --
Col. 15, line 17; "serotoinin," should read -- serotonin, --
Col. 16, line 14; "pharmaceutically acceptable" should read -- pharmaceutically-acceptable --
Col. 16, line 20; "N(H):" should read -- N(H); --
Col. 16, line 20; "pharmaceutically acceptable" should read -- pharmaceutically-acceptable --
Col. 16, line 36; "pharmaceutically acceptable" should read -- pharmaceutically-acceptable --
Col. 16, line 39; delete ";" second occurrence
Col. 17, line 2; "alkyl) means" should read -- alkyl means --.

Signed and Sealed this

Thirteenth Day of October, 1992

Attest:

DOUGLAS B. COMER

Attesting Officer      Acting Commissioner of Patents and Trademarks